United States Patent
Ball et al.

(10) Patent No.: US 10,245,294 B2
(45) Date of Patent: Apr. 2, 2019

(54) DIETARY SUPPLEMENT

(71) Applicant: GRATUK TECHNOLOGIES PTY LTD, Lane Cove North, New South Wales (AU)

(72) Inventors: Malcolm Ball, Lane Cove North (AU); Kent Taylor, Lane Cove North (AU)

(73) Assignee: GRATUK TECHNOLOGIES PTY LTD, North Ryde NSW (AU)

( * ) Notice: Subject to any disclaimer, the term of this patent is extended or adjusted under 35 U.S.C. 154(b) by 0 days.

(21) Appl. No.: 15/318,437

(22) PCT Filed: Jun. 15, 2015

(86) PCT No.: PCT/AU2015/050330
§ 371 (c)(1),
(2) Date: Dec. 13, 2016

(87) PCT Pub. No.: WO2015/188235
PCT Pub. Date: Dec. 17, 2015

(65) Prior Publication Data
US 2017/0119837 A1    May 4, 2017

(30) Foreign Application Priority Data
Jun. 13, 2014  (AU) ................ 2014902247

(51) Int. Cl.
*A61K 36/00*     (2006.01)
*A61K 36/899*    (2006.01)
*A23L 33/22*     (2016.01)
*A61P 29/00*     (2006.01)

(52) U.S. Cl.
CPC ............ *A61K 36/899* (2013.01); *A23L 33/22* (2016.08); *A61P 29/00* (2018.01); *A23V 2002/00* (2013.01); *A61K 2236/00* (2013.01)

(58) Field of Classification Search
CPC .................................................. A61K 36/00
See application file for complete search history.

(56) References Cited

FOREIGN PATENT DOCUMENTS

| | | |
|---|---|---|
| CN | 101032304 A | 9/2007 |
| CN | 101112238 A | 1/2008 |
| CN | 102907584 A | 2/2013 |
| WO | 2007050656 A2 | 5/2007 |
| WO | WO-2007140521 A1 * | 12/2007 ............... A61K 8/97 |
| WO | 2011035381 A1 | 3/2011 |
| WO | 2013131124 A1 | 9/2013 |
| WO | 2013131125 A1 | 9/2013 |
| WO | 2014162303 A1 | 10/2014 |

OTHER PUBLICATIONS

Scurlock et al, Bamboo: An overlooked biomass resource? Biomass and Bioenergy, (2000) vol. 19, No. 4, pp. 229-244.*
International Search Report and Written Opinion for International (PCT) Patent Application No. PCT/AU2015/050330, dated Aug. 11, 2015, 16 pages.
International Search Report and Written Opinion prepared by the Australian Patent Office on Aug. 11, 2015, for International Application No. PCT/AU2015/050330.
Supplemental European Search Report dated Jan. 26, 2018 in EP Application No. 15805905.5.
NutriKane Products, web page https://web.archive.org/web/20140516190615/http://nutrikane.com.au, link dated May 16, 2014, retrieved Mar. 1, 2018, © 2014 NutriKane.
MediKane Natural Medical Products, web page https://web.archive.org/web/20140516194925/http://medikane.com.au, link dated May 16, 2014, retrieved Mar. 1, 2018, © 2014—Medikane.
KFSU Ltd, Product Profile: Kfibre®, https://web.archive.org/web/20140307233639if_/http://www.kfibre.com/user-assets/EMAIL_KFSU_PA_KfibreProfile_3_2012_pdf, Mar. 7, 2014, retrieved Mar. 1, 2018, © 2009-2011 KFSU.

* cited by examiner

*Primary Examiner* — Qiuwen Mi
(74) *Attorney, Agent, or Firm* — Berg Hill Greenleaf Ruscitti LLP

(57) ABSTRACT

Use of dietary fiber material extracted from grasses of the Poaceae family such as sugarcane, sweet sorghum and bamboo for the alleviation of chronic inflammation through improvement in intestinal flora and reduction of pro-inflammatory pathways.

5 Claims, No Drawings

DIETARY SUPPLEMENT

CROSS REFERENCE TO RELATED APPLICATIONS

This application is a national stage application under 35 U.S.C. 371 and claims the benefit of PCT Application No. PCT/AU2015/050330 having an international filing date of 15 Jun. 2015, which designated the United States, which PCT application claimed the benefit of Australian Patent Application No. 2014902247 filed 13 Jun. 2014, the disclosure of each of which are incorporated herein by reference.

TECHNICAL FIELD

The invention relates to the field of commercial food supplement manufacture. In particular, the invention relates to a dietary supplement, the use of said supplement in the diet of an individual, and the method of manufacture of said supplement.

BACKGROUND OF THE INVENTION

Inflammation is a critical and natural biological response in an animal's body to help protect itself from infections, irritants or injuries. There are three types of inflammation that occur in animal systems: acute, chronic and systemic.

Acute inflammation is the body's immediate reaction to injury, be it physical, microbial or toxin related. Chronic inflammation generally involves a stronger reaction that calls on the immune system to fight particularly strong infections or diseases over an extended period. A complex biological cascade of molecular and cellular signals underlies the inflammatory process and the physiological responses.

When any harmful agent first enters the system, pro-inflammatory cytokines, which are the signalling proteins secreted by immune system cells, are released. This alerts the entire immune system to the presence of an unwanted and potentially harmful agent in the body. After an initial inflammation period, inflammation regulators are produced to reduce extended damage to healthy tissue.

Remediation is carried out by simultaneously destroying and healing the inflamed tissues until all affected tissues are gone. In a healthy biological process this serves to internally manage chronic inflammation challenges for a healthy outcome. In some cases, the animal's body can sacrifice some healthy tissue to limit the greater threat caused by the injury.

However, when the inflammatory system is compromised in some way, abnormalities in immune response can create a host of inflammatory disorders. Chronic inflammation becomes a concern when the cycle of inflammation and regulation becomes so extended that healthy tissues are affected, or so that the signals are no longer properly regulated. This can occur through genetic defect, when invasive organisms prove difficult to remove (such as in the case of multi-drug resistant organisms), through environmental influences (such as pro inflammatory diet factors) or as combinations of the above.

Systemic inflammation occurs when unchecked chronic inflammation reaches a critical stage and moves beyond local tissue and into the lining of blood vessels and organs. The specific management and response to this ongoing exposure is determined by complex factors such as genetics, diet, allergies, environmental factors, lifestyle and even mental health. It is the constant biological stress and immune system activity that will result in systemic pro-inflammatory states transitioning to secondary diseases and symptoms. Recently, it has been shown that two of the mechanisms that the body uses to regulate inflammation are dietary antioxidants and maintaining a balanced microbiome that inhibits the growth of pro-inflammatory bacteria. A diet low in essential micronutrients and antioxidants, such as a diet high in processed fat and starchy foods, has been found to promote the growth of pro-inflammatory bacteria. The consumption of such a diet on a regular basis will result in the frequent triggering of the inflammatory state. However, the body may lack the nutrition required to counter the pro-inflammatory signals.

The systemic inflammation response involves a large number of mediators, some of which are used as clinical or diagnostic markers of inflammation or inflammatory disease. One class of mediator bio-molecule that is linked to cell signalling and inflammatory responses is cytokines, a broad category of small proteins. Cytokine's physiological role in inflammatory processes and pathologic role in systemic inflammatory states have been increasingly recognised. Recently published studies on development of early stage type-2 diabetes in animal models describe an inflammatory link via macrophage invasion of pancreatic tissue, thus releasing large quantities of pro-inflammatory cytokines. It is reported that this cytokine response in pancreatic tissue damages the insulin producing beta cells leading to the onset of diabetic states through the immune cell activity.

A sub-class of proteins that play a key role in the innate immune system as well as the digestive system are Toll-like receptors (TLRs). Primarily their activation response is the release of the pro-inflammatory cytokines. The inflammatory response provoked by Toll Like-Receptor activation has led to the thought that endogenous activators of Toll Like-Receptors may hold a causal link to autoimmune disease development. Mounting evidence suggests several TLR subclasses are involved in processes that impair insulin signaling in insulin-responsive organs. In fact, a distinctive feature of obesity is a low-grade level of inflammation, likely originating in the expanding adipose tissue.

The diagnostic tests available to clinicians to measure general levels of systemic inflammation include: C-reactive protein (CRP), Erythrocyte sedimentation rate (ESR), Extractable Nuclear Antigens (ENA), Antinuclear Antibodies (ANA), white blood cell count and albumin levels. All of these tests are non-specific as abnormal levels might result from a condition unrelated to inflammation. Various cytokines and adhesion molecules are not often used in a clinical setting primarily because they are not diagnostic in identifying a source of inflammation in the body.

A number of chronic diseases have inflammatory components, such as Auto-immune diseases, diabetes, gestational diabetes, asthma, diverticulitis, rheumatoid arthritis, atherosclerosis, IBS, chronic fatigue syndrome, psoriasis, IBD, and cancer. Current research has indicated preliminary inflammatory and intestinal health components to Alzheimer's disease, autism, depression and a range of mental disorders, and menopause. The underlying causal mechanism of these diseases is unknown and the role of inflammation in disease pathogenesis is under significant scientific and medical investigation.

Dietary intake is recognised as one of the main mitigating factors of systemic inflammation and has been reported to modulate inflammatory responses within the body. Overall, studies suggest that diets rich in high Glycemic Index (GI) foods (simple sugars and carbohydrates), trans-fats (hydrogenated or partially hydrogenated oils) and saturated fats, tend to stimulate inflammation.

In contrast, a diet rich in monounsaturated fatty acids from olive oil, fruits and vegetables, nuts, beans, and whole plant grains has been shown to reduce inflammation. Studies investigating links between dietary fibre, low GI foods and inflammatory responses are further revealing the bi-directional relationship between the host immune system and gut micro-flora. It has been reported that dietary fibre supplementation may provide a strategy for manipulating the intestinal bacterial profile, changing the interaction with the mucosal immune system, thereby modulating the host immune system.

Essential fatty acids play a role in the body's inflammatory processes. Increasing the dietary intake of omega-3 fatty acids (eicosapentaenoic acid (EPA) and docosahexaenoic acid (DHA)) found in oily fish and fish oils, as well as some marine plants, generally decreases Inflammatory markers (IM) whereas an increase in the dietary intake of omega-6 fatty acids has been observed to increase IM's. The specific ratio of omega-6 to omega-3 fatty acids has been researched with a typical western diet consisting of approximately 16:1 Omega-6 to Omega-3. However it is estimated that humans evolved with an omega fat ratio closer to 1:1 and this may be a worthwhile dietary target to reduce inflammatory responses in the body.

Current research links phytochemicals, polyphenolic compounds, catechins, specific vitamins and minerals to the therapeutic reduction of inflammation associated diseases. Some reports links natural spices and herbs to direct inhibition of pro-inflammatory pathways. Traditionally, herbs and spices have been used to increase antioxidant and micronutrient quantity in a diet.

The mechanisms of all these nutritional effects, both positive and negative, are now being primarily focused in the gut health of the host. Gut health will refer to the normal function, shape, size and permeability of tissues in the stomach, small intestine (Duodenum, Jejunum, Ileum), large intestine (Caecum, colon, Rectum). Each of these regions of the gastrointestinal tract has mucosal and sub-mucosal linings that govern nutrient passage. Along the entire tract resides the largest collections of foreign cells in the human body, both in variety and total numbers. These microbial populations are referred to as the microbiome or 'the ecological community of commensal, symbiotic, and pathogenic microorganisms that literally share our body space'.

Studies now link Type-I diabetes as an autoimmune disease that is correlated with a multiplicity of predisposing factors, including aberrant intestinal microbiome, a permeable intestinal mucosal barrier, and intrinsic differences in immune responsiveness. It has been stated by proponents in the medical community that up to 70% of the immune system is underneath the bowel lining, and that the immune system is significantly affected when partially digested food particles can pass through the bowel wall. Additionally, mouse studies are indicating links between a dysfunctional microbiome and diabetes, gastrointestinal diseases, asthma, allergy and obesity. The interaction of the microbiome with the immune system, as mediated by the gut, likely plays a vital role in the development and treatment of many inflammatory and autoimmune diseases.

Nutritional intake is becoming more recognised as a corrective action to restore a dysfunctional microbiome to normality. Nutritional treatments are recognised not only as a preventative to inflammatory conditions an effective alternative to pharmaceutical drugs without the adverse side effects of many pharmaceuticals.

As an example of a causal link to dietary intake in auto-immune conditions, it is becoming accepted that gestational diabetes has a significant relationship to nutrition, and it has been suggested that many cases of gestational diabetes may be treated with nutritional supplements or a targeted nutritional diet.

People who suffer from all types of diabetes mellitus, (Type I, II & LADA-Latent Auto-Immune Diabetes in Adults) have been found to have a higher incidence of other chronic conditions than the general population including inflammation caused by oxidative stress and gastro-intestinal disorders. This means that the presence of potential food allergies and/or malabsorption can play a major role in the selection of diet control for diabetic individuals. Common food allergies and intolerances of diabetes sufferers have been reported with respect to wheat, dairy, soy, and oats (amongst others). It has been estimated that 2% of the general population suffers from food allergies however diabetics are reported to have increased risk of developing food allergies and intolerances. Large scale cohort studies of multiple ethnicities and lifestyles have shown that regardless of other factors (such as genetic predisposition and body weight) a "healthy" diet has a statistically significant improvement on outcomes both for diabetes mellitus itself and secondary correlating diseases.

The proportion of individuals suffering an autoimmune & inflammation related conditions is clearly on the rise, with an associated correlation to the modern western diet. Emerging research suggests that digestive abnormalities may be the underlying cause of degenerative gut health and many auto-immune diseases.

Accordingly, it is an object of the invention to introduce a food ingredient to the diet of individuals that are at risk or suffering chronic systemic inflammatory and auto-immune conditions initiated, or adversely affected, by poor digestive health, that assists in ameliorating the underlying inflammatory mechanism and reducing symptoms.

SUMMARY OF THE INVENTION

According to one aspect of the invention, there is provided the use of dietary fibre material extracted from grasses of the Poaceae family (sugarcane, sweet sorghum, and/or bamboo) in the manufacture of a food product that is formulated to ameliorate the effects of inflammatory states that may increase the risk or lead to auto-immune responses, or chronic inflammatory diseases in the body. The resulting food product is high in total dietary fibre and stable micro-nutrients.

Preferably, the Poaceae grass fibre is prepared via a process including the steps of: subjecting the plant material to at least one wet diffusion step to separate unwanted macronutrients (carbohydrates, fats and proteins) from a residual fibre material whilst maintaining micro-nutrient content; and subjecting the residual fibre material to a drying process that does not induce significant breakdown of the bioactive macro and micro nutrients retained by the chemical free extraction. This process may be either rapid high temperature, low-heat drying process, or a controlled slow drying process at temperatures below 50° C. In a high-temperature, low-heat drying process, the exposure time is preferably less than 10 seconds. Either process may thereby retain the biologically active molecules in the fibre, and to enhance the water retention properties of said residual fibre product.

There are a number of advantages to using dietary fibre material extracted from one of the grasses in the way described above. Firstly, the products are mostly allergen free (no adverse allergic effects have ever been recorded with sugarcane or sorghum, and allergies to bamboo are extremely rare). Also, these fibre sources have been shown to improve gut lining health over and above other sources of fibre. They contain benefits of both soluble and insoluble fibre and have ratios of fibres that more accurately represents natural—whole plant foods than other products. They can also be high in other micronutrients such as iron and can have the ability to protect antioxidants. Unlike many forms of dietary fibre, high dietary fibre foods prepared from Poaceae family grasses utilise the actively growing stem of the plant. Thus, these foods are produced from active vegetable matter utilising multiple micronutrients such as antioxidants and minerals (which are retained by the present process) rather than dormant, non-food parts of the plant such as seed husks. Additionally, many other sources of dietary fibre, such as inulin or fibre produced from bagasse, require chemical or heat treatment, which removes or destroys active micronutrients, In the art, dietary fibre benefits have been confused by the definition of dietary fibre. In general, it has been shown that diets that are high in 'total dietary fibres', i.e. those coming from natural vegetable sources, provide greater health benefits than those that are either highly processed or come from non-food sources such as the husks of various seeds. Without wishing to be bound by theory, it is believed that a carbon source alone may be insufficient for significant health improvement. Rather, a combination of dietary fibre and useable micronutrients may benefit both the microbiome and the host human alike.

Using fibres separated from sugarcane as an example these fibres have several advantageous properties compared to incomplete (not whole plant fibres) such as bran, psyllium husk and inulin. The fibre is a true lignose, hemicellulose and cellulose combination such as the total dietary fibres found in most vegetables. Additionally even though sugarcane fibre is classed as almost entirely insoluble fibre, using the standard chemical methods of classification, it has many of the properties of soluble fibres as well such as it has a high water binding capacity (up to 8-10 times by weight) and a prebiotic effect. Also even though insoluble fibres are known to have little or no effect on blood glucose levels it has been observed that, when prepared correctly, sugarcane fibre can have profound benefits on postprandial and fasting blood glucose levels. This is most likely a combination of the fact that the hemicellulose fraction of the fibre has soluble components that are released during digestion and that when prepared correctly the fibre retains a number of biologically active molecules.

This fibre not only has the effect of reducing postprandial blood glucose levels and lowering the Glycaemic Index (GI) of foods, but when prepared and formulated correctly can be used to produce foods that have continued beneficial effects on fasting glucose levels and a long term reduction in hyperglycaemia related complications. The beneficial effect of this invention is not limited to the reduction of high blood glucose levels; it may also be used to reduce the risk of hypoglycaemia by being included in energy rich foods for improved overall control of BGLs in diabetic and pre-diabetic individuals.

In addition, when this fibre source is prepared via the process as described herein, the fibre tends to retain its functionality with respect to treating inflammation to a greater level, due to the retention of biologically active molecules in the fibre. The fibre source also provides the correct dietary fibre level to address this condition in the majority of the population. By playing an active role in the encouragement of beneficial microbial populations as well as restricting pathogenic microbes, mega-grass fibres are able to reduce inflammation caused by the waste and break down products of the microbiome. Additionally there is strong evidence to suggest that many highly processed foods act as inflammation promoters through mimetic activation of pro-inflammatory receptors such as the TLR systems. It is further known that whole plant fibres, such as those found in these grasses, tend to reduce or inhibit these negative interactions.

The invention also allows more flexible product formats to be developed, in particular that allow individuals suffering conditions involving complications other than inflammation to address to deficiency in their own way, especially when provided with the correct type of fibre in a relatively easy-to-use format. Individuals no longer have to rely on food manufacturers to generate high fibre, high nutrient foods that they can eat.

Preferably, the wet extraction step is a diffusion extraction, done under relatively low-shear conditions. The optimal wet extraction step temperature is in the range 25° C. to 70° C. The wet extraction technique can be done with or without a pressing step prior to drying so long as the fibre and juice are steeped for sufficient time is allowed for binding of the micronutrients to the fibre matrix.

According to another aspect of the invention the base fibre matrix may be enhanced using fruit or vegetable juices that are processed in conjunction with the grass of choice. In the same manner as simple grass processing the nutrient rich solution is allowed to steep in a chemical free water diffusion step, at low temperatures (preferably between 25-70° C.). The process may then include a cold press or go straight to drying using either a high temperature short residence time, or low temperature longer air dry to produce a fibre matrix that includes macro and micronutrients from one grass and one or more fruit and/or vegetable sources. This allows interaction between more than one nutrient and fibre pool through the same process further enhancing the anti-inflammatory properties of the resultant products According to another aspect of the invention, there is provided a food product formulated to ameliorate the effects of inflammation and associated conditions; said food product containing dietary fibre material extracted from sugar cane, sweet sorghum or bamboo, said dietary fibre material preferably having been prepared according to the steps defined above.

According to another aspect of the invention, there is provided a method of treatment of the effects of chronic inflammation and associated conditions in an individual by feeding to said individual a food product incorporating dietary fibre material extracted from sugar cane, sweet sorghum or bamboo; said dietary fibre material preferably having been prepared according to the method defined above.

Now will be described, by way of particular, non-limiting examples, preferred embodiments of the invention.

DETAILED DESCRIPTION OF THE INVENTION

The current invention takes advantage of the properties of a dietary fibre isolate produced from grasses from the Poaceae family, such as sugar cane, in such a way that maximised retention and minimal destruction of the bioactive molecules occurs.

The method of preparation of the fibre material from sugar cane is broadly similar to that described in WIPO patent document no. WO2011/035381 by KFSU Pty Ltd, which is incorporated herein by reference. However, the process according to the present invention may be defined as having the following essential features:
1. A sugar cane size reduction step;
2. A relatively 'gentle' aqueous extraction stage that separates the fibre from other grass fractions, including the sugar fraction in the case of sugarcane or sweet sorghum, without causing degradation of the fibre functionality; and
3. A relatively gentle drying step that minimises degradation of the fibre functionality. The drying step may either use higher temperatures for very short periods of time or temperatures below 50° C. for longer times, in either case enough energy is supplied to evaporate the water without providing sufficient energy to significantly denature labile bioactive molecules such as antioxidants and vitamins.
4. The procedure may also include a co-processing step whereby other high value raw ingredients such as certain fruits and vegetables are subjected to the same procedure allowing the non-grass bioactive molecules to be incorporated and stabilised by the final product.

It is preferred that the extraction step be an aqueous diffusion extraction performed at a relatively neutral pH. It is also preferred that the drying step be either a rapid vortex drying operation that, as may be achieved via a low temperature, vortex dryer, such as that supplied by Tensei in Japan, or by super-dried pre-cooled air such as that supplied by a counter current ambient air drying apparatus.

It is understood that adequate dietary fibre, and high quality vitamins and antioxidants are important to the healthy function of the digestive system. It is also known that dietary elements such as non-digestible carbohydrates can have an influence on both the microbial populations and the inflammation states of the intestinal track that can either positively or negatively influence the likelihood of developing digestive health issues such as irritable bowel syndrome in humans. It is also thought that human diets tend to be deficient in dietary fibre, and other essential micronutrients and/or use fibre sources known to cause allergies, intolerances and inflammation events, such as wheat, inulin and psyllium husks.

While the use of dietary fibres for general bowel health and constipation relief is common there is mounting evidence that fibre sources that are 'incomplete' (i.e. not 'from a vegetable source but either come from grains, or are highly processed or chemically modified) have more limited benefits than previously thought. It is further understood that many sources of fibre that were thought to have a beneficial effect may in fact exacerbate inflammatory conditions either directly (through immune response) or indirectly (through the suppression of benign micro-flora and/or the encouragement of pathogenic micro-flora).

It has also been shown that in many cases extraction and purification of micronutrients that have been shown to have a beneficial effect on diets and inflammation either lose their benefit or have those benefits greatly reduced. It is thought that this is due to loss of essential co-factors and synergistic effects, as well as the fact that many of these nutrients (such as vitamins and antioxidants) are acid labile and do not safely pass through the hydrolytic environment of the stomach without the protection found in a whole plant source. The process described herein is therefore designed to maintain these micronutrients in a form that maintains high activity levels.

The invention provides for the use of Poaceae grass fibres such as those found in sugarcane in the formulation of foods or diets that seek to reduce the risk of development of inflammation conditions, or which ameliorate the symptoms of those conditions, if acquired. When prepared according to the invention, these fibre sources, and the foods incorporating them, have a number of advantages over other fibre sources and food, including that:

they are relatively hypoallergenic;
they contain both insoluble and soluble fibre in beneficial proportions for dietary intake;
they contain a number of bioactive molecules that beneficially affect microbial populations and inflammation levels to improve intestinal health to a greater degree than other fibre sources;
They can be prepared in a 'chemical-free' manner and contain no harmful trace elements, unlike fibre from other sources such as chemically modified starch;
They are entirely in their natural state and do not contain modifications such as cross linkages, or partially hydrolysis which are known to be pro-inflammatory agents.
They can be prepared in such a way as to retain the micronutrients and active molecules found in the liquid fraction of the grasses, without the need to extract and purify those components for their biological function;
The grasses contain components such as, polyphenols and certain high quality dietary fibres that have all been shown to aid in improving the health of the intestinal wall and combat inflammation. This product combines these elements in a natural food that has been processed in a manner that retains beneficial effects and allows for synergistic action;
The product can be combined with other sources of nutrients known to be beneficial to inflammation and intestinal health in other natural sources and stabilise and combine them in a manner that allows further synergistic benefits
Other inventions have sought to isolate the various components however the combined effects of the components exceed that of individual extracts. Additionally the "whole food" nature of the products limits side effects and protects from overdose;

It is also known that too much fibre in the diet can have several negative side effects including but not limited to constipation, diarrhoea and bad flatulence. In one embodiment, where the fibre product is added as a supplement to an individual's diet, dietary fibre intake can be more easily controlled.

The supplement is also classed as a natural food which is increasingly important to many consumers.

The embodiments of the invention can take a number of forms, each with several advantages for users.

In this document:
A 'carrier' is a palatable substrate for the core fibre, which may or may not contain protein or other nutrients; including but not limited to: fruit extracts, broths, purees, dairy products, baked goods; and which may be in solid or liquid form.
'Inert filler' is any product used to increase the bulk size of fibre according to the invention to allow for ease of handling by the user. The filler may contain flavours or nutrients, and other dietary fibres to improve mouth feel, but does not necessarily contribute to the total benefit provided by the invention.
'Pellet' includes any compact form of the invention, including but not limited to:
A dried pill or tablet in the manner of a vitamin.
A soft lolly style lozenge that may be used as a treat or as an addition to other foods A product compacted with flavour and mouth-feel components designed to separate and suspend into a liquid medium such as water or juice.

All of the examples below can optionally be formulated with additional vitamins and bioactive molecules, or sweeteners such as stevia. Preferably any added nutrients would be sourced from natural ingredient so that a "natural" descriptor may be maintained for the final product.

Example 1

In this example, 0.5-2.0 g of the active fibre is added to a flavouring medium and pressed into a pellet. Each pellet contains sufficient fibre and bioactive molecules to improve intestinal integrity and improve digestive health whilst reducing the inflammation state of the subject. The pellets are prepared at a formulation level such that the dose may be varied if the consumer has been placed on a high fibre diet by their physician. However, if there is no other dietary control, the nature of the product means the dose may be increased without negative effects. The pellet may be taken during or immediately before or after a meal.

Example 2

In this example the active fibre is mixed with a flavoured drink (for example fruit juice or milk) and pasteurised for sterility (1-5 g per 100-250 ml). A drink prepared in this manner is a convenient, ready-to-consume product to be taken with meals. Carriers and inert fillers may be added to the product to generate a favourable experience for the subject.

Example 3

In this example the supplement is prepared as an easy-to-measure powder with flavours, stabilisers and inert filler, formulated specifically to be combined with water. Specifically, the active fibre could be mixed with a dry flavour component and an inert filler to form easy-to-use granules. The dose (1-5 g) would be in a convenient single-serve sachet or in a multi-dose bulk pack. This example is best suited to aid weight loss as the granules can be mixed with water (thereby allowing less food to be consumed each meal). The product can be formulated with low carbohydrate content as this is often a requirement for individuals that are using diet to control unwanted gut flora blooms. Additionally other high quality nutritional ingredients (such as vegetable extracts) may be added to increase the bioactive load of the drink.

Example 4

In this example the supplement is prepared in a solid flavoured meal such as a biscuit or a bar (1-5 g per ready mixed food). Multiple biscuits can be consumed by an individual to provide a specific dosing regimen as needed for their lifestyle. This has two advantages over other delivery systems in that it feels more like a treat for the subject, and it eliminates the need for liquid, makes it easier to eat anywhere and eliminates any other sources of potential inflammation (such as acidic juices or high sugar drinks). Specifically these foods can take 2 forms either:
1) The biscuit can be prepared without significant carbohydrate and sugars. This form would be used as a complement to a meal to provide a dose without affecting nutritional load in its own right.
2) The biscuit is formulated with a defined carbohydrate, fat and protein dose to provide a "meal replacement" serve. Ideally this format would include other components known to reduce inflammation, or at the very least to have a neutral effect on inflammation levels. This would include hypoallergenic sources and some natural supplements. This product could then be used to more tightly control food intake for those with severely compromised systems.

Example 5

In this example the fibre material is supplied as an ingredient for other manufacturers of high-fibre foods for the intestinal health/hypoallergenic food industries. This example provides several benefits for potential food manufacturers/suppliers:
If the fibre material is used to replace allergenic fibres such as wheat or psyllium husks then the product may be labelled as hypo-allergenic. The fibre can improve beneficial microbial populations while also reducing the carbohydrate content of foods which may increase the malignant microbial populations.
The fibre material supports the use of "all natural" marketing claims for the foods.
The fibre material provides other health benefits compared with other fibre sources, allowing the food manufacturer to potentially make more substantive claims.
The water retention capacity of the grasses of the Poaceae family, prepared as described above, is far greater than many commercial insoluble fibre sources. By using the active fibre in foods the manufacturer can reduce calorific content per unit mass of food. This may also result in a significant commercial saving for the manufacturer.

Example 6

The sugarcane fibre produced using the inventive process for human consumption was analysed for the presence of antioxidants. Polyphenolics and flavonoids were found at levels equivalent to or greater than those found in many fresh fruits and in stable form at room temperature. Naturally present selenium is a natural antioxidant present at 2.4 mg/kg (12.92% RDI) in a stable form.

Food products and methods according to the invention make use of the unique qualities of Poaceae family grass crops, particularly whole sugarcane, that have been prepared using a chemical-free, low-heat procedure. This makes it easy and convenient to use while still retaining the beneficial nutrients and bioactive molecules in the food.

The following examples relate to the therapeutic benefits of the product used in the present invention.

Example 7

A faecal sample was obtained and prepared as an inoculum in a gut mimicking solution. The faecal inoculum was introduced to the gut mimicking medium as a control and also to gut mimicking medium containing the sugarcane fibre. Both were then incubated for 72 hrs at 37° C. At time points 0, 4, 24, 48, 72 hrs an aliquot was removed for 16S RNA analysis to determine the changes to the bacterial population. Three species of fibre digesting bacteria were notably maintained increased across the 120 hr period compared to the control. Three species of inflammation inducing bacteria were inhibited or supressed across the 72 hr period compared to the control. This represents a modification to the simulated microbiome of upregulating advantageous and down regulating non-advantageous bacterial populations.

Example 8

Premise: Inflammatory disorders are associated with increased activity of NF-Kb and AKT, two of the main mediators of this process.

Approach: Ethanol extracted sugar cane fibre and resveratrol (positive control) were administered to LPS-stimulated SW480 colon carcinoma cell line for multiple time points (1, 2, 4 and 12 hours). Cell lysates were analysed by western blotting of the phosphorylated version of these two proteins (active) and normalised with their corresponding total protein expression.

Preliminary outcomes: Ethanol extracted sugar cane fibre inhibits the activity of NF-Kb and AKT in 30% after 4 and 12 hours of treatment. On the other hand, resveratrol is observed to decrease the expression of AKT only.

Example 9

An individual living with a thyroid condition that results in inflammation around the eyes consumed 7 g per day of a sugarcane fibre product according to the invention. The individual noted that swelling and soreness around the eyes was markedly reduced and general eye strain experienced was improved during the period of consumption.

Example 10

An individual presented with gastrointestinal disorders resulting in significant inflammatory effects and periodic bleeding and inflammation related paralysis. The subject was weened onto a sugarcane fibre product according to the invention at 7 g per day. Within 10 days, the individual reported reduction of bleeding events and gastrointestinal discomfort. After 3 months of consuming the sugarcane fibre product according to the invention at 7 g per day, the individual reported that the product was the source of the reduction in inflammation and was more successfully managing the symptoms experienced. At one point in the usage of the product, consumption was ceased for approximately 2 weeks. The individual reported that inflammatory symptoms were returning until supplementation with the sugarcane fibre product according to the invention was reintroduced.

Example 11

An individual presented with long term digestive symptoms related to intestinal bloating, gas and inflammation. Consumption of 3.5 g sugarcane fibre product according to the invention was commenced. At 7 days, the individual reported a marked reduction in the bloating and inflammatory gastrointestinal experience. At 3 months, the individual noted a reduction/periodic cessation of the medication that was being used to manage the oesophageal and gastrointestinal inflammation.

In the following detailed case studies, a sugar cane fibre product according to the invention was used to alleviate a number of intestinal health conditions that have known inflammatory components.

Case Study 1—Rehabilitation Outcomes in Persons with Spina Bifida, Royal Melbourne Hospital Spina bifida (SB) encompasses a range of congenital neural tube defects, with an annual incidence of 1 per 1000 live births worldwide (7 per 10,000 live births in Australia).[1] SB related impairments (such as neuromuscular weakness, neurogenic bladder or bowel, hydrocephalus, cognitive impairment, bone or joint deformity, insensate skin etc.) can cause limitation in 'activity' (reduced mobility, self-care ability, cognitive dysfunction) and 'participation' (employment, study, family and social reintegration) (4, 7).[2,3] As disease progresses, other issues surface, such as degenerative musculoskeletal issues, cardiopulmonary disease, obesity, bowel and bladder issues, latex sensitivity and others.[2,4] These disabilities can have a cumulative effect in this patient population, reduce their quality of life (QoL) and can cause considerable distress. Persons with SB require concurrent rehabilitation for longer-term management in conjunction with medical and surgical management.[5,6] Rehabilitation provides medically supervised patient-centred interdisciplinary (ID) care delivered by various health disciplines that maximise activity and participation.

A randomised controlled trial (RCT) was conducted to assess the effectiveness of a structured ID rehabilitation program to improve disability and participation in an adult SB population in the Royal Melbourne Hospital (RMH), a tertiary referral centre in Victoria, Australia. The RMH has the only state-wide ID clinic in Victoria to address the many disabilities faced by young adults with SB as they transition from paediatric to adult services. They are referred from public and private clinics across the state and enrolled in the SB transitional clinic database held at the RMH in conjunction with the Department of Health, Victoria. A total of 54 adult patents with SB were randomized to a treatment group (n=27) for high intensity rehabilitation program (with cognitive-behaviour therapy), or a control group (n=27) comprising usual care. The ID rehabilitation program included 30 minute blocks of individual therapy sessions, 2-3 times per week for 6 weeks. These comprised a physical reconditioning program, wheelchair and seating evaluation, task reacquisition skills and whole body adaptive techniques. Participants in the treatment group, in addition to the ambulatory rehabilitation program, received individualised ID care with intensive focus on education for self-management, continence and skin care, and a cognitive-behaviour program for an additional 4-6 weeks beyond the usual program. Within the ID rehabilitation program, continence care included: an individualised bladder management program and structured bowel program: sugarcane fibre-supplements (manufactured according to the invention, such as "Nutrikane™", manufactured by Medikane Pty Ltd), where necessary, laxatives and anal irrigation as appropriate provided by nursing and medical staff for faecal continence. Participants' assessments were at baseline (T1 before intervention), at 3-months post-intervention (T2) using validated questionnaires.

Participants were predominantly female (57%), average age 33 years. With bowel and bladder dysfunction reported by one-third of all participants. As a part of the structured bowel management program, all participants in the treatment group were provided with additional fibre supplement ('Nutrikane™'). At 3-months post-treatment follow-up (T2), both bowel and bladder function improved significantly in the intervention group compared with the control group, with moderate to large magnitude in outcome measures. The treatment group compared with the control group, also showed a significant reduction in psychological distress, and improved QoL at 3-months follow-up. At 3-months follow-up, just over half (55%) participants reported continued use of the fibre supplement (Nutrikane™). The reported reason behind this discontinuation included: consistency, taste, hard to swallow and difficulty in preparation. The participants also suggested that they will continue to take fibre supplement (Nutrikane™) in future, if the product quality (taste, consistency) improved. None of the participants reported any adverse effects related to the program or fibre supplement. The findings suggest that a comprehensive, coordinated clinical approach targeting specific symptoms (such as bowel/bladder symptoms) and cognitive-behaviour strategies for self-management, coping and psychological adjustment; improve symptoms, psychological problems and enhance overall quality of life of persons with SB.

Case Study 2—Structured Bowel Management Program in Inpatient Rehabilitation, Royal Melbourne Hospital Bowel dysfunction is common in hospitals and in the community, with faecal incontinence (FI) affecting approximately 2% and constipation affecting one-third of the adult population. Establishing an effective bowel and bladder regime is essential for wellbeing of patients. A range of interventions are recommended for bowel management for inpatients in rehabilitation, such as: dietary recommendations, laxatives, anorectal/perianal stimulation, timed performance of bowel routine with food intake (gastro-colonic and recto-colonic reflexes), and pharmacological agents.

The Royal Melbourne Hospital (RMH), a tertiary referral centre in Victoria has a 52 bed rehabilitation inpatient unit and specialises in neurological rehabilitation (e.g. MS, GBS, developmental disabilities, strokes, tumours, head injury, spasticity management), oncological, amputee, chronic pain and orthopaedic/musculoskeletal rehabilitation. The current Rehabilitation Continence Service at RMH aims to provide multi-disciplinary clinical expertise in the assessment, management and education (including self-management) for patients experiencing bladder and/or bowel dysfunction. As part of ongoing inpatient multidisciplinary rehabilitation program and quality improvement initiative, the structured bowel management program (SBMP) (integrated within current ward practice) was implemented. This program was provided by an interdisciplinary treating team, comprising a rehabilitation physician, nurse, physiotherapist, occupational therapists, and a dietician. The aim of the SBMP was to assist patients in achieving adequate and timely bowel movements using methods appropriate to their disease process and tailored for specific clinical needs. This included: comprehensive assessment, management (pharmacological, diet, fibre-supplements (such as sugar cane fibre supplement "Nutrikane™"), where necessary, physical procedures (enema, biofeedback, manual evacuations etc.).

A prospective longitudinal study was conducted to evaluate this program and to assess the patient perception/compliance and effect on the bowel dysfunctions of fibre supplements, including "Nutrikane™". Overall, 100 patients participated in the study. Each patient was assessed for bowel dysfunction on admission and the SBMP was instituted based on an individuals' clinical need. The assessments were at baseline (T1), and discharge from ward (T2) using validated questionnaires. Program evaluation was conducted at 3-month (T3) post-discharge.

Participants were predominantly female (52%), with average age of 68 years. Almost one-half (43%) had neurological conditions and remaining musculoskeletal problems (41%). At admission 62% reported bowel dysfunction, mainly constipation (82%) and FI (11%). Overall, 89 participants were provided with additional fibre supplement ('Nutrikane™'). At discharge (T2) participants showed significant improvement in bowel habit and stool consistency, severity of bowel symptoms, and overall quality of life. In addition, patients' functional ability and cognitive function improved significantly. Eighty-nine participants participated in the 3 months post-discharge telephone follow-up (T3). Of these, 86 (96%) participants were satisfied with the bowel management program and continued to follow protocol recommendations. Seventy-six (85%) indicated that their bowel function improved or has been stable. Interestingly, only 28 (31%) participants continued to take the fibre supplement (Nutrikane™); 34% had ceased taking any form of fibre supplements, the remainder either switched to another form of fibre supplement or were taking supplements intermittently. The reported reason behind discontinuation of the fibre supplement included: consistency, taste, hard to swallow and difficulty in preparation. The participants also suggested that they will continue to take fibre supplement (Nutrikane™) in future, if the product quality (taste, consistency) improved. None of the participants reported any adverse effects related to the program or fibre supplement. The findings suggest that evidence-based SBMP including additional fibre supplements can improve bowel symptoms and enhance overall quality of life in patient admitted to rehabilitation settings. Bowel management should be a priority within rehabilitative services.

The products and methods address several problems associated with poor fibre consumption, as well as having a positive impact on digestive health, while also contributing to the elimination of the potential problems of intolerance and malabsorption in individuals that suffer allergies or intolerances to common fibre sources. The product may also be classed as a natural, whole food; meaning it does not have some of the problems associated with many pharmaceutical treatments, including some negative side effects.

REFERENCES

1. Foster M R. Spina bifida. 19 May 2014 [cited 2014 10 Nov.]; Available from: http://emedicine.medscape.com/article/311113-overview#a0156.
2. Spina Bifida Association. Spina Bifida: a guide for medical professionals. [cited 2014 10 Nov.]; Available from: http://www.spinabifidaassociation.org/atf/cf/%7B85f88192-26e1-421e-9e30-4c0ea744a7f0%7D/A%20GUIDE%20FOR%20MEDICAL%20PROFESSIONALS.PDF.
3. Singhal B, Mathew K M. Factors affecting mortality and morbidity in adult spina bifida. Eur J Pediatr Surg 1999; 9 Suppl 1: 31-32.
4. Webb T S. Optimizing health care for Adults with Spina Bifida. Dev Disabil Res Rev 2010; 16: 76-81.
5. Mitchell L E, Adzick N S, Melchionne J, Pasquariello P S, Sutton L N, Whitehead A S. Spina bifida. Lancet 2004; 364: 1885-1895.
6. Royal Australian College of General Practitioners. Overview of Spina Bifida and the nervous system. Australian Family Physician 2002; 31: 7-9.

The invention claimed is:

1. A method of treatment of the effects of chronic inflammation and associated conditions in an individual by feeding to said individual a food product incorporating dietary fibre material derived from whole sugar cane, whole sweet sorghum or whole bamboo; said dietary fibre material having been prepared according to a method including the steps of:

subjecting the dietary fibre material to at least one wet diffusion step at neutral pH and a temperature is in the range of 25° C. to 70° C., to separate unwanted macronutrients including carbohydrates, fats and proteins, from a residual fibre material of the dietary fibre material whilst maintaining bioactive micro-nutrient content including polyphenolic antioxidants and flavonoid antioxidants; and subjecting the residual fibre material to a drying process that does not induce significant breakdown of the bioactive micronutrients retained by the chemical free extraction.

2. The method of claim 1, wherein said drying process is a rapid, low-heat drying process capable of retaining bioactivity of the bioactive micronutrients in said residual fibre material, and to enhance water retention properties of said residual fibre material.

3. The method of claim 2, wherein an exposure time of said residual fibre material to the drying process is less than 10 seconds.

4. The method of claim 1, wherein the drying process is a controlled slow drying process at a temperature below 50° C., capable of retaining the bioactivity of the bioactive micronutrients in said residual fibre material, and to enhance water retention properties of said residual fibre material.

5. The method of claim 1, wherein the wet diffusion step is a diffusion extraction, done under relatively low-shear conditions.

* * * * *